United States Patent [19]
Franseen et al.

[11] Patent Number: 5,470,228
[45] Date of Patent: Nov. 28, 1995

[54] EDGEWISE ORTHODONTIC BRACKET

[75] Inventors: Steve A. Franseen, Denver; Jeffrey A. Peterson, Aurora, both of Colo.

[73] Assignee: RMO, Inc., Denver, Colo.

[21] Appl. No.: 60,879

[22] Filed: May 12, 1993

Related U.S. Application Data

[63] Continuation-in-part of PCT/US92/04263, May 20, 1992.

[51] Int. Cl.⁶ .................................................. A61C 3/00
[52] U.S. Cl. ............................ 433/8; 433/10; 433/13; 433/18
[58] Field of Search ....................... 433/8, 9, 10, 11, 433/12, 13, 14, 16, 18

[56] References Cited

U.S. PATENT DOCUMENTS

| | | | |
|---|---|---|---|
| 1,890,487 | 12/1932 | Angle . | |
| 3,435,527 | 4/1969 | Kesling . | |
| 3,854,207 | 12/1974 | Wildman | 32/14 |
| 4,103,432 | 8/1978 | Kessel | 32/14 |
| 4,193,195 | 3/1980 | Merkel et al. | 433/13 |
| 4,219,617 | 8/1980 | Wallshein | 433/8 |
| 4,242,085 | 12/1980 | Wallshein | 433/14 |
| 4,260,375 | 4/1981 | Wallshein | 433/11 |
| 4,386,908 | 7/1983 | Kurz | 433/9 |
| 4,478,577 | 10/1984 | Warren, Jr. | 433/18 |
| 4,498,867 | 2/1985 | Kesling | 433/16 |
| 4,527,975 | 7/1985 | Ghafari et al. | 433/8 |
| 4,545,760 | 10/1985 | Forster | 433/18 |
| 4,669,981 | 6/1987 | Kurz | 433/9 |
| 4,712,999 | 12/1987 | Rosenberg | 433/8 |
| 4,793,804 | 12/1988 | Schudy | 433/8 |
| 4,799,882 | 1/1989 | Kesling | 433/8 |
| 4,819,316 | 4/1989 | Rossini et al. | 433/8 |
| 4,820,151 | 4/1989 | Pospisil | 433/17 |
| 4,859,179 | 8/1989 | Kesling | 433/8 |
| 4,917,602 | 4/1990 | Broussard | 433/8 |
| 5,030,089 | 7/1991 | Kawaguchi | 433/8 |
| 5,062,794 | 11/1991 | Miura | 433/10 |
| 5,125,831 | 6/1992 | Pospisil | 433/8 |
| 5,125,832 | 6/1992 | Kesling | 433/8 |
| 5,127,828 | 7/1992 | Suyama | 422/8 |
| 5,154,607 | 10/1992 | Hanson | 433/8 |
| 5,160,261 | 11/1992 | Peterson | 433/8 |
| 5,161,969 | 11/1992 | Pospisil et al. | 433/8 |
| 5,320,525 | 6/1994 | Förster | 433/8 |
| 5,322,435 | 6/1994 | Pletcher | 433/8 |

FOREIGN PATENT DOCUMENTS

| | | | |
|---|---|---|---|
| 0379668 | 8/1990 | European Pat. Off. | 433/10 |
| 0389223 | 9/1990 | European Pat. Off. . | |
| 2497657 | 7/1982 | France | 433/8 |
| 9107925 | 6/1991 | WIPO | 433/10 |

OTHER PUBLICATIONS

3M Unitek Corporation Catalog (Copyright 1990), pp. 1-1, 1-3, and 3-7.
Ortho Organizers, Inc. Advertisement "Journal of Clinical Orthodontics", Sep. 1989.

*Primary Examiner*—Cary E. O'Connor
*Attorney, Agent, or Firm*—Sheridan Ross & McIntosh

[57] ABSTRACT

An improved edgewise orthodontic bracket is disclosed. In one embodiment, a bracket (10) comprises a single pair of opposing T-shaped tie wings (12, 14) which define an archwire slot (18) therebetween. Notches (20) are provided on each of the mesial and distal sides of the center leg (28) of each T-shaped tie wing (12, 14) for selectively receiving a ligating device. The notches (20) are defined in the gingival/occlusal edges of the tie wings (12, 14) and comprise sloped portions (24) that extend labially towards the archwire slot (18). Convex sidewall portions (42) and convex floor portions (44) are provided in the archwire slot (18) adjacent to the notches (20). An auxiliary slot (70) may be centrally disposed under the center legs (28) of the opposing T-shaped tie wings (12, 14). Alternatively, twin auxiliary slots (80) may be disposed under the convex archwire slot floor portions (44). An integral T-shaped hook (50) may be provided as a cantilevered extension from the center leg (28) of one of the T-shaped tie wings (12, 14) for use in attachment of traction devices.

27 Claims, 7 Drawing Sheets

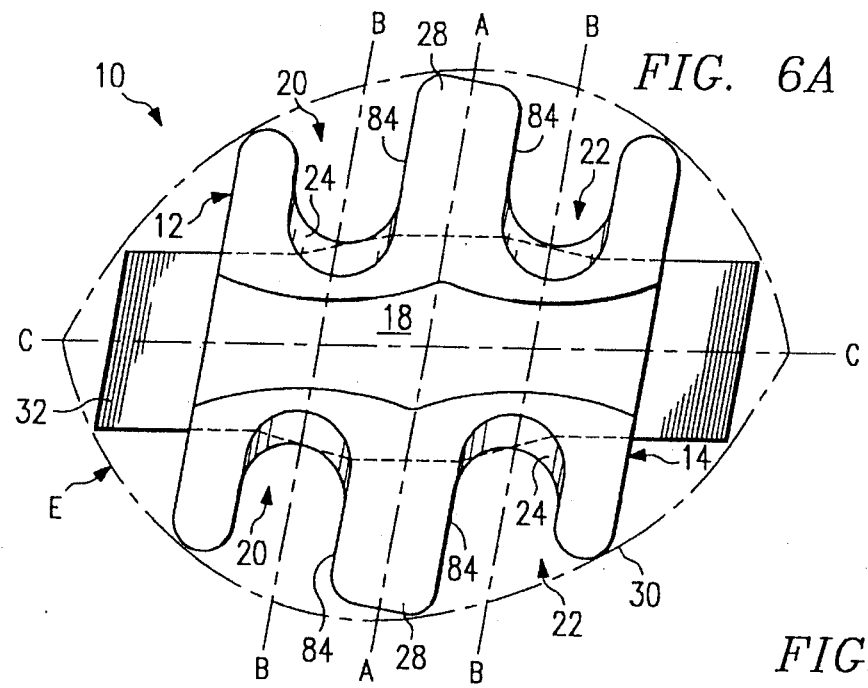
FIG. 6A
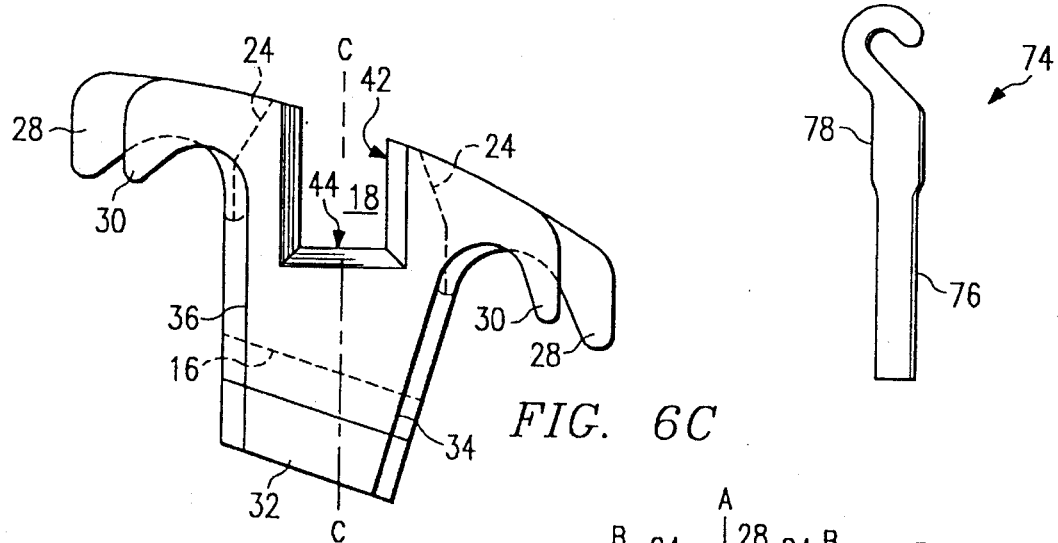
FIG. 6C
FIG. 7A
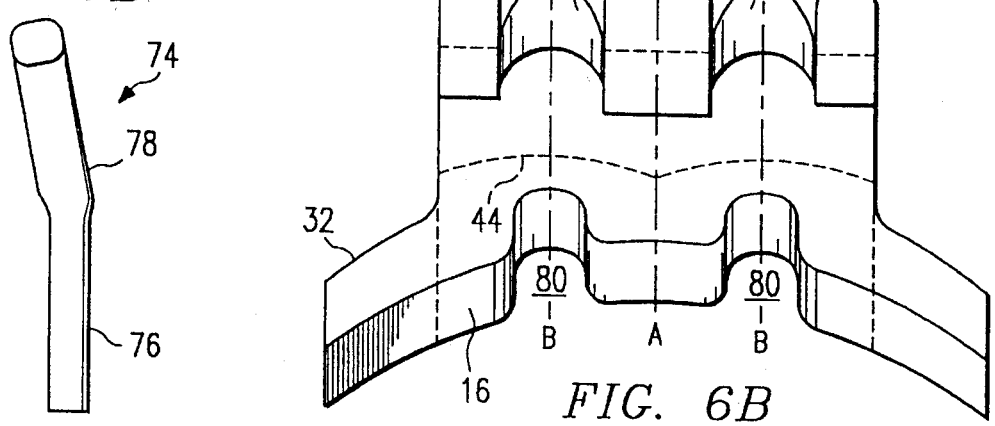
FIG. 7B
FIG. 6B

EDGEWISE ORTHODONTIC BRACKET

RELATED APPLICATIONS

This application is a continuation-in-part of international application No. PCT/US92/04263, filed May 20, 1992, which claims priority from U.S. Pat. No. 5,160,261, issued Nov. 3, 1992.

FIELD OF THE INVENTION

This invention generally relates to edgewise orthodontic brackets and, more particularly, to edgewise brackets having enhanced treatment, comfort and ease-of-use features, as well as increased modalities.

BACKGROUND OF THE INVENTION

Orthodontic brackets are widely used to align teeth through the application of forces selectively provided by interconnected archwires and accessories. Brackets are typically of metal, ceramic or composite construction and are interconnected to either bands or bonding pads for attachment to teeth.

In edgewise brackets, an archwire passes through a labially opening, horizontal slot defined by one or more pair of opposing tie wings. The archwire is preshaped and sized to provide the desired forces. In each bracket, a tie wing pair includes a gingivally extending tie wing and occlusally extending tie wing. Once placed in the slot of one or more pair of tie wings, an archwire is typically restricted therein by a ligating device such as a steel or elastomeric ligature.

As orthodontic treatment objectives and techniques continue to evolve, numerous corresponding edgewise bracket designs and interconnecting accessories have been proposed. Recently, it has been recognized that it is desirable to reduce frictional engagement between the archwire and bracket surfaces defining the archwire slot to facilitate space closure and bodily tooth movement. Similarly, in many situations, it is now a goal to reduce frictional engagement between the archwire and ligating device employed to restrict the archwire within the slot. Such friction reduction can markedly increase the rate of tooth movement and reduce the duration of the orthodontic treatment.

At the same time, patient comfort and ease-of-use considerations have become increasingly important. Patient comfort has been largely addressed by reducing bracket size to yield smaller and more smoothly contoured brackets. Ease-of-use considerations have stimulated bracket designs which facilitate practitioner's bracket placement/use and accommodate plural modalities.

The present invention represents significant advances in relation to the above-noted orthodontic bracket considerations, both singularly and combinatively, while maintaining the structural integrity of the bracket.

SUMMARY OF THE INVENTION

In one aspect of the present invention, an edgewise bracket is provided having a pair of tie wings defining an archwire slot therebetween, and a pair of ligating support means, one defined within the mesial/distal extent of each tie wing. The ligating support means may be selectively employed to reduce frictional engagement between an archwire positioned in the slot and a ligating device positioned on the ligating support means and across the archwire slot. Each ligating support means includes a sloped, or angled, portion that extends labially toward the slot (e.g., labially from the gingival/occlusal periphery towards the slot), to reduce binding of a ligating device positioned thereupon. The ligating support means are preferably notches extending from the gingival or occlusal periphery of a tie wing, sized to readily receive a ligating device, and preferably having a curvlinear, concave configuration to further reduce binding. Typically, the opposing notches in a given pair of tie wings will have a common center axis which is parallel to the gingival-occlusal center axis of the bracket. When the archwire slot includes convex sidewall and/or floor portions to reduce archwire/bracket frictional engagement, the ligating support means are preferably disposed adjacent thereto (e.g., centered upon a common gingival-occlusal plane) for enhanced treatment control.

In another aspect of the present invention, an edgewise bracket is provided having a single pair of tie wings and two pairs of opposing ligating support means defined within the mesial/distal extent of the tie wings, one pair on each of the mesial and distal sides of the bracket. The gingival/occlusal extremes of the tie wings define an elliptical configuration when viewed from the labial ("viewed labially"). More particularly, each tie wing comprises central, mesial and distal portions which extend gingivally or occlusally, with ligating support means defined between the central and mesial portions and between the central and distal portions, wherein the gingival/occlusal edges of such portions define an elliptical configuration. Such configuration accommodates size reduction, yielding patient comfort benefits, while preserving structural integrity and performance.

In this regard, and as will become apparent, a single pair of opposing T-shaped tie wings is preferred. That is, the "caps" of the T-shaped tie wings define an archwire slot therebetween, and the "center legs" of each tie wing extends gingivally or occlusally. The ligating support means are preferably notches defined on the gingival/ occlusal periphery on both the mesial and distal sides of a center leg of each T-shaped tie wing. The center legs each comprise a gingivally/occlusally extending cantilevered portion that can be conveniently employed as a stanchion for ligature interconnection. The mesial/distal tie wing tip portions on the outside of each notch also comprise gingivally/occlusally extending cantilevered portions that extend a sufficient distance outward from the outer tie wing sidewalls to retain a ligating device in an arcuate seat formed under the cantilevered tie wing tip portions and center legs during conventional ligation. Relatedly, the cantilevered center leg of each T-shaped tie wing should extend at least approximately the same distance outward beyond the outer gingival/occlusal extremes of the adjacent ligating support means so as to retain a ligating device when the ligating support notches are selectively employed by a practitioner to support a ligating device.

In a further aspect of the present invention, an edgewise bracket is provided having a single pair of tie wings defining an archwire slot therebetween, and an integral T-shaped hook extending gingivally/occlusally (typically only gingivally) from one tie wing, and in perpendicular relation to the longitudinal center axis of the archwire slot, wherein traction devices (e.g., rubber bands, springs, etc.) can be readily attached from a plurality of directions so as to accommodate plural modalities for treatment. The T-shaped hook is centered upon the gingival-occlusal center axis of the bracket, and is preferably provided as a cantilevered extension of the center leg of a T-shaped tie wing so as to communicate external force moments created by inter-connected traction devices close to a tooth's root center of resistance. Preferably, the T-shaped hook is generally flat as viewed from the mesial and distal aspects. Further, as viewed from the labial aspect, the T-shaped hook preferably comprises a tapered portion contiguous to the center leg of the T-shaped tie wing, an arcuate neck portion contiguous thereto, and a head portion contiguous thereto the tapered portion, wherein a traction device may be reliably maintained in the neck portion. That is, the tapered portion serves to restrict movement of the traction device towards the archwire slot of the bracket, and the head portion serves to restrict disconnection of the traction device from the T-shaped hook. The integral T-shaped hook preferably comprises a malleable material so as to allow for selective pivotal movement of the T-shaped hook by the orthodontic practitioner as may be desirable for soft tissue clearance and patent comfort.

In yet another aspect of the present invention, an edgewise bracket is provided having at least one pair of tie wings defining an archwire slot therebetween, wherein when viewed from mesial/distal aspects, the gingivally/occlusally facing outer sidewalls of the tie wing pair define a trapezoid. One outer sidewall is disposed at an angle relative to the longitudinal center plane of the archwire slot, wherein the sidewall extends labially away from such center plane. The other sidewall is disposed substantially parallel to the archwire slot center plane. The angled sidewall is typically disposed gingivally in both maxillary and mandibular applications. By way of example, use of the described configuration and positioning allows for enhanced, early treatment of partially erupted upper bicuspids, wherein the archwire slot will be acceptably, gingivally positioned upon full eruption of the bicuspid. This enhances treatment and reduces demands upon the practitioner time. Further, bracket systems of this design will generally reduce bracket/tooth contact between the upper and lower arches. Bracket profile and strength can also be acceptably maintained using the described configuration. The benefits associated with this trapezoidal configuration may be extended to orthodontic treatment applications requiring positive, negative, or no torque by appropriately configuring/contouring the occlusal/gingival extent of the bracket base or bottom.

In another aspect of the present invention, an edgewise bracket is provided having one tie wing pair defining an archwire slot therebetween and at least one auxiliary slot extending from a gingival edge to the occlusal edge, or vice versa, wherein the slot and shaft of the auxiliary device to be inserted into the slot have complimentary configurations to restrict rotational movement therebetween. By way of example, the auxiliary slot may have adjoining flat inner sidewalls (e.g., defining square corners), and the auxiliary shaft may have complimentary flat outer sidewalls (e.g., defining square corners), wherein rotational movement therebetween is desirably restricted.

In a related aspect of the present invention, an edgewise bracket is provided having a single tie wing pair defining an archwire slot therebetween, at least one convex portion extending labially and transversely across the floor of the archwire slot, and at least one auxiliary slot extending gingivally/occlusally and positioned under the convex slot floor portion. By positioning the auxiliary slot under the convex slot floor portion, bracket height can be advantageously conserved, and therefore reduced, so as to enhance patient comfort. When two convex slot floor portions are provided, one on each of the mesial/distal sides, twin auxiliary slots may be advantageously positioned so that one passes under each of the convex slot floor portions. In addition to the above-noted advantages, this bracket yields significant tooth rotation capabilities. For example, in early treatment stages, the twin auxiliary slots can be utilized with a steel ligature to achieve rapid gross tooth rotation. As can be appreciated, complementary auxiliary slot/auxiliary shaft configurations of the above-described nature can also be employed.

In one embodiment of the present invention, an edgewise bracket is provided having a single set of opposing T-shaped tie wings with ligating support notches defined on each side (i.e., mesially and distally) of the center leg of each tie wing. The sidewalls defining the archwire slot are provided to present two sets of opposing convex sidewall portions, one set on each of the mesial and distal sides of the bracket. Similarly, the floor of the archwire slot is provided to present two convex portions extending labially and transversely across the slot, one on each of the mesial and distal sides of the bracket. By virtue of this arrangement, the bracket yields desirable tooth rotation and alignment capabilities with reduced archwire/archwire slot frictional engagement and selectively reduced archwire/ligating device frictional engagement. Further, this configuration defines a dynamic archwire slot, wherein the archwire is allowed to maintain a "memory" of its slot entry angle, as is now desirable. The notches each comprise a portion that extends labially outwardly from the gingival/occlusal periphery towards the archwire slot and presents concave, curvlinear surfaces to reduce ligature binding. The gingival/occlusal edges of the center legs and wing tip portions of the opposing T-shaped tie wings define an elliptical configuration when viewed labially so as to reduce bracket size and advance patient comfort/appearance. All prominent edges exposed to soft tissue are preferably rounded for patient comfort.

An integral T-shaped hook of the above-described nature may be optionally provided as a cantilevered gingival/occlusal extension of the center leg of either T-shaped tie wing. The T-shaped hook preferably comprises a malleable material and preferably comprises flat lingually and labially facing surfaces, wherein the hook can be manually pivoted to a limited extent by a practitioner relative to the center leg of the tie wing.

An auxiliary slot may also be optionally provided and disposed within the gingival-occlusal center plane of the bracket, underlying the center leg portions of the opposing T-shaped tie wings. Alternatively, twin auxiliary slots may be provided, one on each side of the gingival-occlusal center plane of the bracket (i.e., mesially and distally positioned), such slots passing under the mesial and the distal convex slot floor portions of the archwire slot. Whether a single or twin auxiliary slot arrangement is provided, each slot preferably has an inner-configuration which will restrict rotation of complimentary auxiliaries inserted thereto, as described above.

The T-shaped tie wings of the bracket may also be optionally defined so that the outer gingival/occlusal facing sidewalls of the tie wing pair define a trapezoid when viewed from the mesial or distal aspects. More particularly, one of the outer sidewalls is disposed at an angle relative to the longitudinal center plane of the archwire slot, and may be perpendicular to the tie wing base surface or base/bottom surface of the bracket. The other outer sidewall is disposed in parallel relation to the center plane of the archwire slot.

In combination with the above-described trapezoidal configuration, the base surface of the bracket, namely its gingival/occlusal extent, may be provided for generating "positive torque," "negative torque," and "no torque". "Positive torque" is applied to a tooth having a tooth-long axis which projects the crown outwardly from a plane which is perpendicular to the occlusal plane and which coincides with the respective arch (e.g., mandibular or maxillary) (e.g., when the tooth root is tipped lingually). "Negative torque" is applied to a tooth having a tooth-long axis which projects the crown inwardly from the above-described plane (e.g., when the tooth root is tipped buccally). "No torque" is applied to a tooth having a tooth-long axis which is properly within the above-described plane.

The configuration of the base surface of the bracket, namely its occlusal/gingival extent, may be defined in relation to a reference plane which coincides with that portion of the floor or bottom of the archwire slot which engages the archwire when positioned therein (e.g., a plane which is tangent to the two convex portions on the floor of the slot). As an example of the foregoing trapezoidal configuration and base variations, with the "angled" outer sidewall being gingivally positioned in a maxillary application, the base may be configured to generally extend from its gingival edge to its occlusal edge generally toward the noted reference plane to provide for a "positive torque" on the tooth. Moreover, the base may be configured to generally extend from its gingival edge to its occlusal edge generally away from the noted reference plane to provide for "negative torque" on the tooth. Furthermore, the base may be configured to generally extend from its gingival edge to its occlusal edge generally parallel to the noted reference plane to provide for "no torque" on the tooth. With the "angled" outer sidewall being gingivally positioned in a mandibular application, the above-described non-parallel configurations of the base would provide negative and positive torque, respectively.

The center leg of each T-shaped tie wing may also be optionally disposed at an acute angle relative to the longitudinal center axis of the slot. Such angling may be desired in applications wherein the central axis of the clinical crown is positioned at an acute angle relative to the occlusal plane in normal occlusion. Such angling correspondingly facilitates the practitioner's placement of the bracket on a tooth, wherein the axes of the center legs may be disposed along a tooth long axis, and wherein the center axis of the bracket slot may be disposed parallel to the occlusal plane. Preferably, the mesial/distal facing edges of the center leg of each T-shaped tie wing are also parallel to the axes of the center legs to further facilitate accurate placement on a tooth. It is also preferable for the center axes of opposing ligating support notches to be disposed parallel to the gingival-occlusal center plane of the bracket. Relatedly, for rotational purposes, it is preferable for the apices of the opposing convex slot sidewall portions and a convex slot floor portion correspondingly positioned on the same mesial or distal side to lie within a common plane that is disposed substantially perpendicular to the longitudinal center plane of the archwire slot.

As will be appreciated by those skilled in the art, the embodiment of the invention described herein yields numerous advantageous features, yielding a new state-of-the-art bracket.

BRIEF DESCRIPTION OF THE DRAWINGS

FIGS. 6A–C illustrate labial, side and opposing end views of the modified embodiment of the present invention illustrated in FIGS. 4A–C, with an angulated gingival-occlusal center axis and twin auxiliary slots; and, FIGS. 7A–B illustrate two views of an exemplary auxiliary device useable with the auxiliary slots of the present invention.

DETAILED DESCRIPTION

Figure 1A:
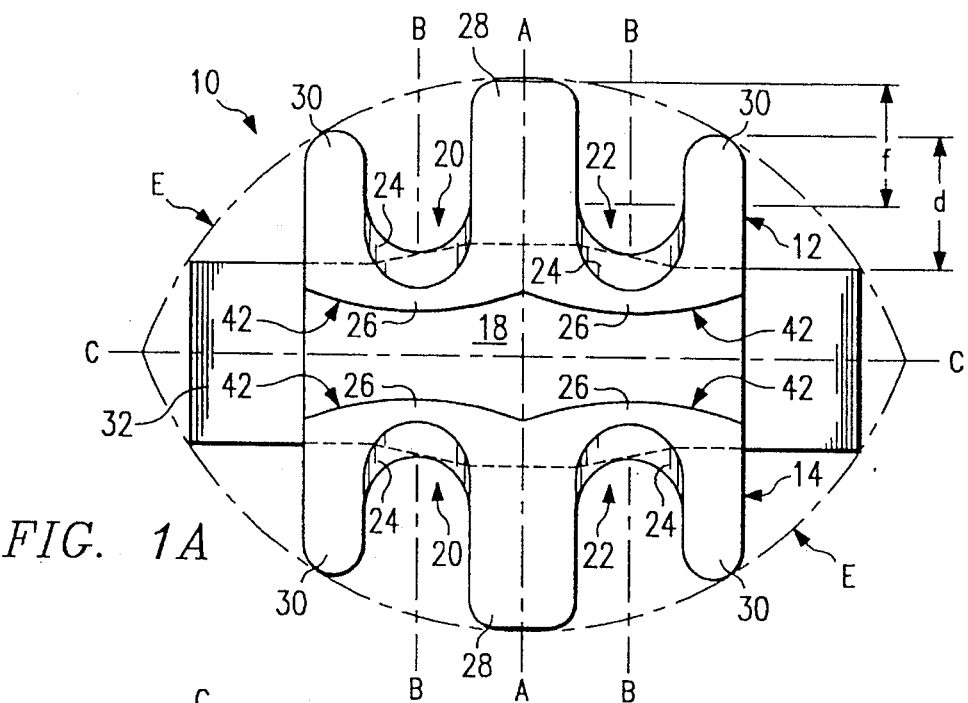
FIGS. 1A–C illustrate labial, side and end views of one embodiment of the present invention.

One embodiment of the edgewise bracket 10 of the present invention is illustrated in FIGS. 1A–C and 2A–D, with various modifications, modalities and an exemplary auxiliary reflected by FIGS. 3A–C, 4A–E, 5A–D, 6A–C and 7A–B. Corresponding features are referenced by common reference numerals.

The edgewise bracket 10 comprises two integral, opposing T-shaped tie wings 12 and 14 having a common base portion and base surface 16, and defining an archwire slot 18 therebetween. By way of example only, a flange 32 may be adjoined to the bracket 10 for subsequent attachment to a band. Alternatively, the bracket may be adjoined to a bonding pad (not shown).

Two sets of opposing ligating support means 20 and 22, are provided, each set comprising a gingivally disposed notch and occlusally disposed notch on the gingival and occlusal edges of tie wings 12, 14, respectively. Each ligating support means has a sloped portion 24 and top land portion 26. The sloped portions 24 have concave, curvlinear surfaces.

Each of the T-shaped tie wings 12, 14 comprises a cantilevered central leg portion 28 centered upon the gingival-occlusal center axis (lying within plane AA) of the bracket 10 and cantilevered mesial/distal wing tip portions 30, with the above-noted top land portions 26 integral therebetween. The gingival/occlusal extremes of the center leg 28 and mesial/distal wing tip portions 30 of the tie wings 12, 14 define, from the labial aspect, an elliptical configuration E. In this regard, cantilevered wing tip portions 30 extend a sufficient distance d outward from the outer sidewalls 34, 36 of the tie wings 12, 14, respectively, to retain a ligating device in an arcuate seat 38 formed under the cantilevered tie wing tip portions 30 and center legs 28. Relatedly, the cantilevered center leg 28 of each T-shaped tie wing 12, 14, extends a distance f beyond the outer gingival/occlusal extreme of the ligating support means 20 adjacent thereto, such distance f being at least approximately as great as the distance d.

Figure 1C:
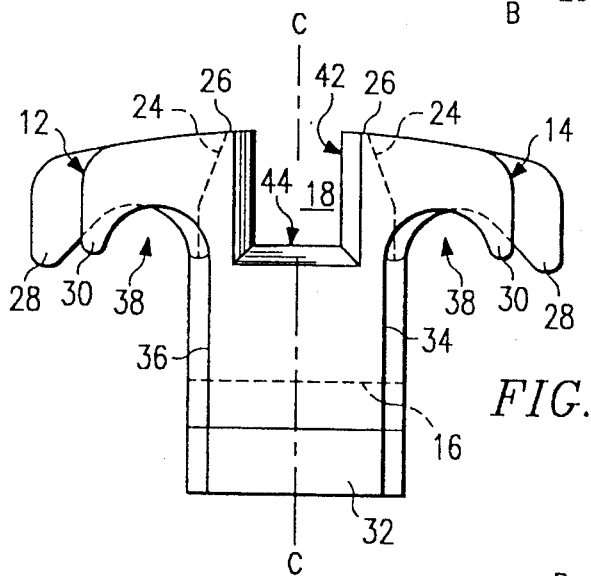
Figure 1B:
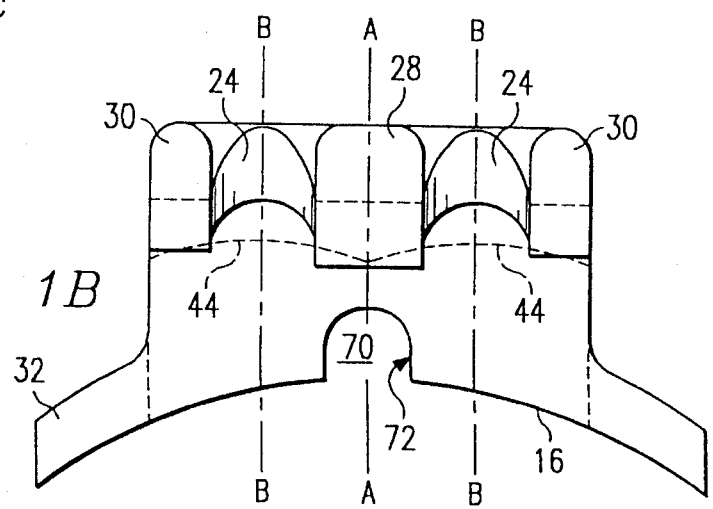

The sidewalls defining the archwire slot 18 comprise two sets of opposing convex portions 42 to reduce frictional engagement with an archwire. Similarly, the floor of archwire slot 18 is provided with two convex portions 44 extending transversely across the archwire slot 18 to reduce frictional engagement with an archwire. As illustrated in FIGS. 1A–C, the ligating support means 20, convex slot sidewall portions 42, and convex slot floor portion 44 disposed on the same side of the gingival-occlusal center plane AA may have a common center axis (lying within plane BB). As such, frictional engagement between an archwire and the slot walls and base, and between an archwire and ligating device supported on ligating support means 20 occurs in a limited region about plane BB.

An optional auxiliary slot 70 may be provided to receive a complimentary auxiliary device, such as the exemplary auxiliary 74 illustrated in FIGS. 7A and 7B. The inner sidewalls of auxiliary slot 70 and interfacing shaft portion 76 of the exemplary auxiliary 74 are preferably configured to restrict rotational movement therebetween. As illustrated, a complimentary square-angled configuration may be employed. Additionally, the auxiliary 74 preferably comprises an extending portion 78 having an outer configuration which will not fit into auxiliary slot 70, thereby facilitating placement and removal.

Figure 2A:
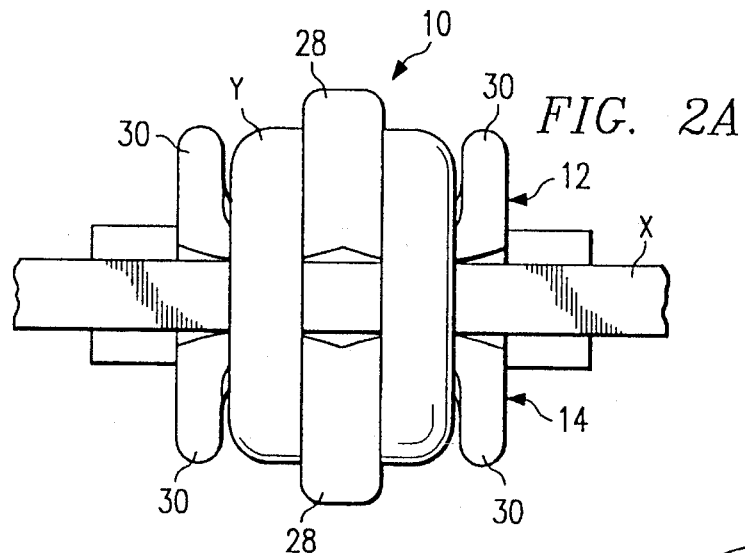
FIGS. 2A and 2B, and FIGS. 2C and 2D, illustrate labial and end views of the embodiment of FIGS. 1A–C when ligating support means are employed to support an elastomeric ligature and when ligating support means are not employed to support an elastomeric ligature, respectively.
Figure 2B:
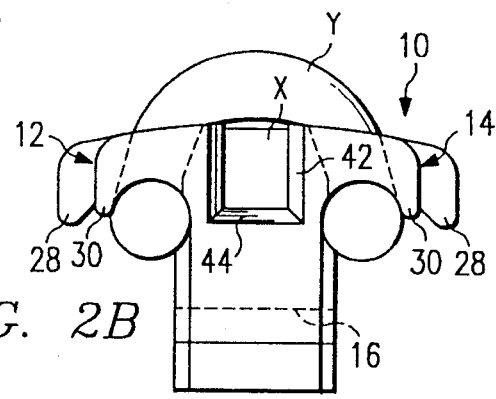
Figure 2C:
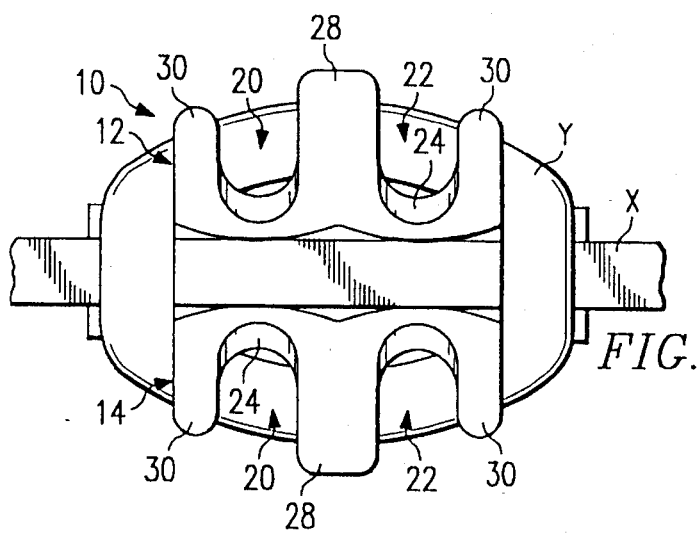
Figure 2D:
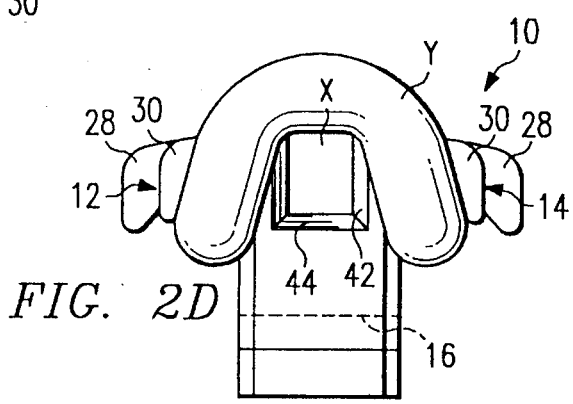

FIGS. 2A–B illustrate the interface between an archwire X and elastomeric ligating device Y when both sets of the ligating support means 20 of the embodiment of the present invention illustrated in FIGS. 1A–C are utilized. FIGS. 2C–D illustrate the interface between an archwire X and elastomeric ligating device Y when neither of the ligating support means 20 of such embodiment are utilized. As will be appreciated by those in the art, there are different treatment situations where each of these modalities may be desired. Additionally, the provision of a set of ligating support means 20 on each of the mesial and distal sides of the bracket 10 allows a practitioner to utilize one set but not the other, as may be desirable.

Figure 3A:
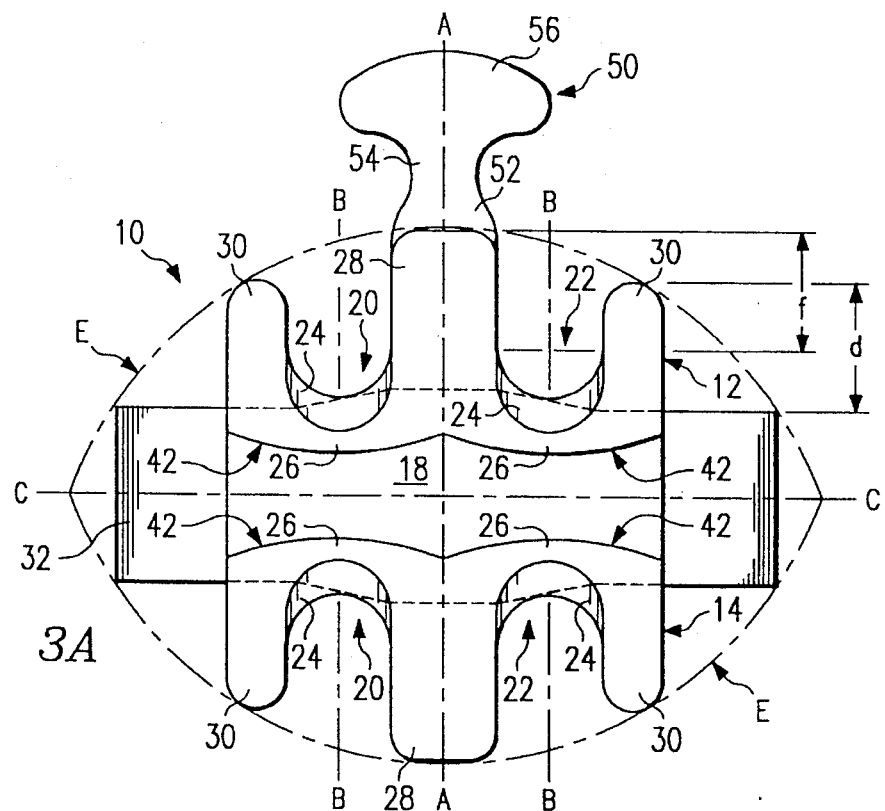
FIGS. 3A–C illustrate labial, side and end views of a modified version of said embodiment of the present invention having an integral T-shaped hook and twin auxiliary slots.
Figure 3C:
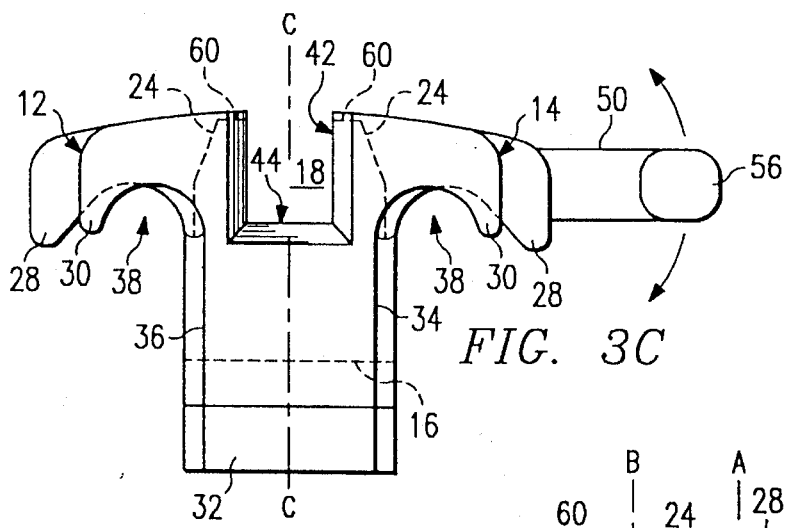
Figure 3B:
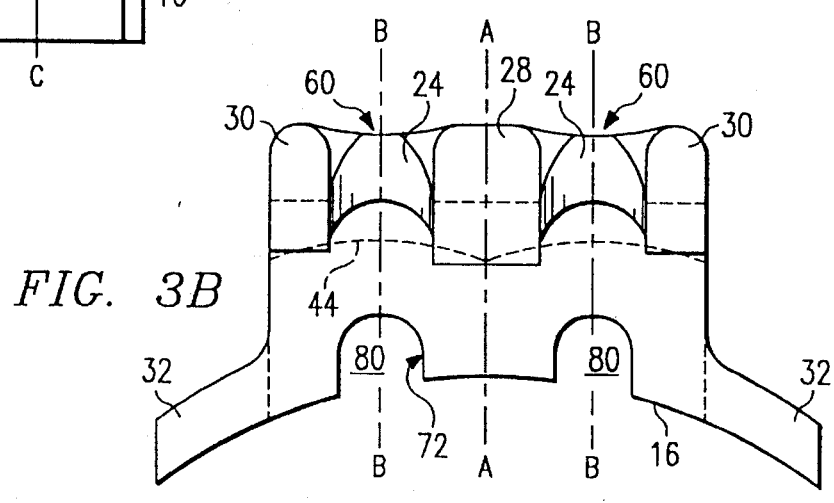

In FIGS. 3A–C an integral T-shaped hook 50 is provided as an extension to the center leg 28 of one of the T-shaped tie wings 12. The T-shaped hook 50 preferably comprises flat lingual and labial surfaces (see FIG. 3C), and is preferably malleable to allow for pivotal movement relative to center leg 20. The T-shaped hook 50 preferably comprises a tapered portion 52, arcuate neck portion 54 and head portion 56, whereby retention of a traction device in neck portion 54 is enhanced.

Twin auxiliary slots 80 may be optionally provided for receipt of an auxiliary device, such as the exemplary auxiliary 74 shown in FIGS. 7A–B. The twin auxiliary slots 80 are beneficially disposed under the convex slot floor portions 44. The configuration of slots 80 and exemplary auxiliary 74 may be as described above to restrict rotational movement therebetween and facilitate placement/removal.

FIGS. 3A–C also illustrate optional saddles 60 which can be provided in the support landing portions 26 for receiving a ligating device. It is believed that such saddles 60 may be beneficial in certain early treatment situations for purposes of retaining an undersized archwire in the desired position for rotational purposes.

In FIGS. 4A–E, the outer sidewall 34 of tie wing 12 and outer sidewall 36 of tie wing 14 define a trapezoid therebetween. Specifically outer side wall 34 is angled relative to the longitudinal center plane CC of the archwire slot 18, and the outer tie wing sidewall 36 is disposed in parallel relation to the center plane CC of the archwire slot 18. By virtue of this arrangement, the outer sidewall 34 may be, for example, advantageously disposed gingivally on partially erupted upper bicuspids. Further, bracket systems employed by this configuration will generally reduce bracket/tooth contact between upper and lower arches.

Figure 4A:
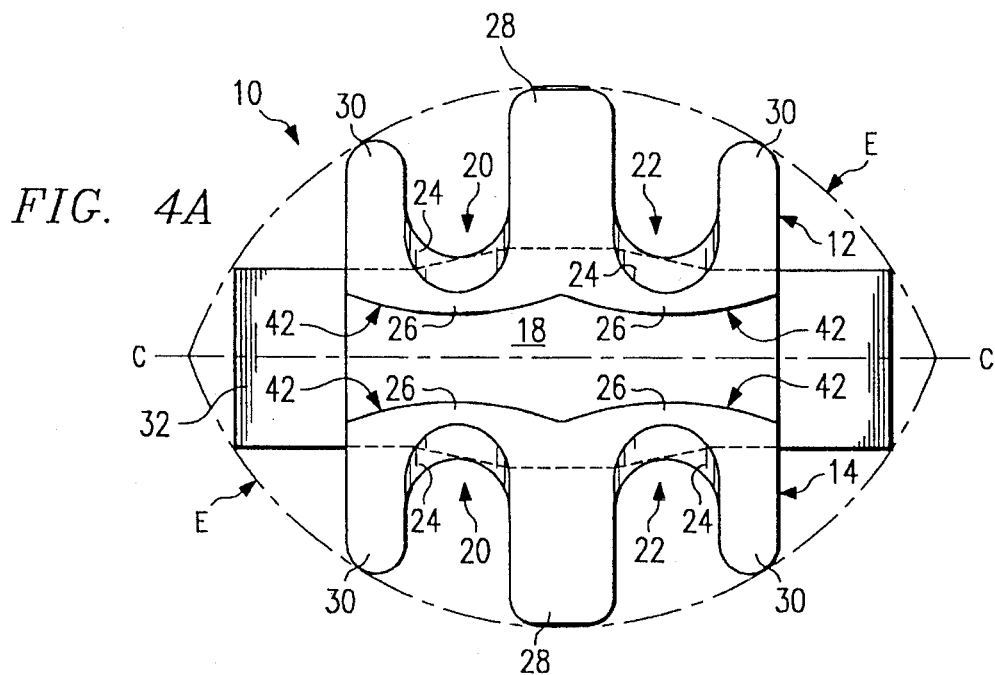
FIGS. 4A–E illustrate labial, side and end views of a modified version of said embodiment of the present invention having outer tie wing sidewalls that define a trapezoid therebetween, the end views illustrating various alternative configurations of the base to provide for positive, negative, and no torque on a tooth.
Figure 4C:
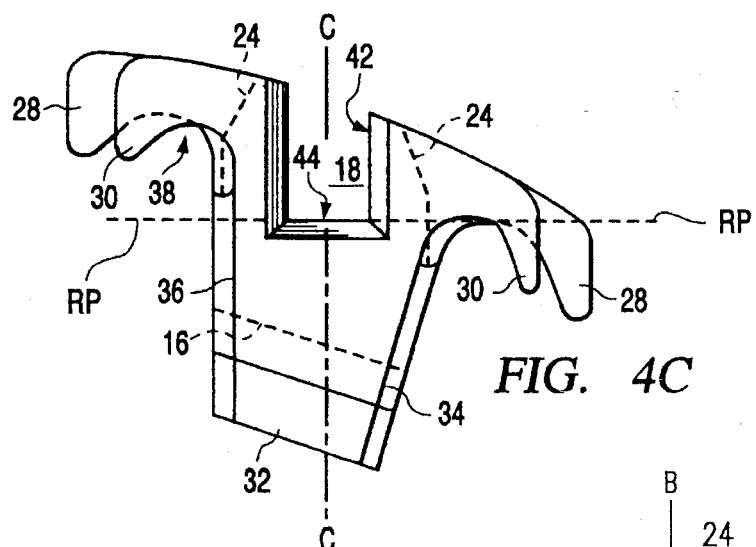
Figure 4B:
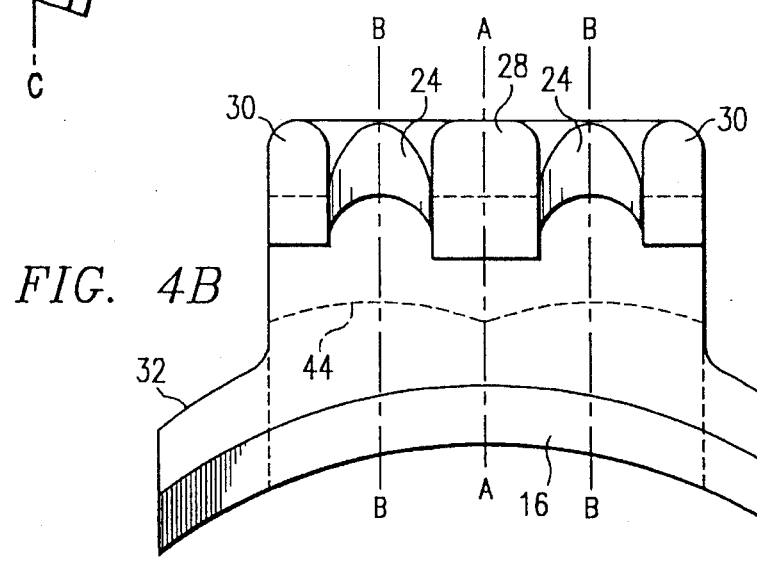
Figure 4D:
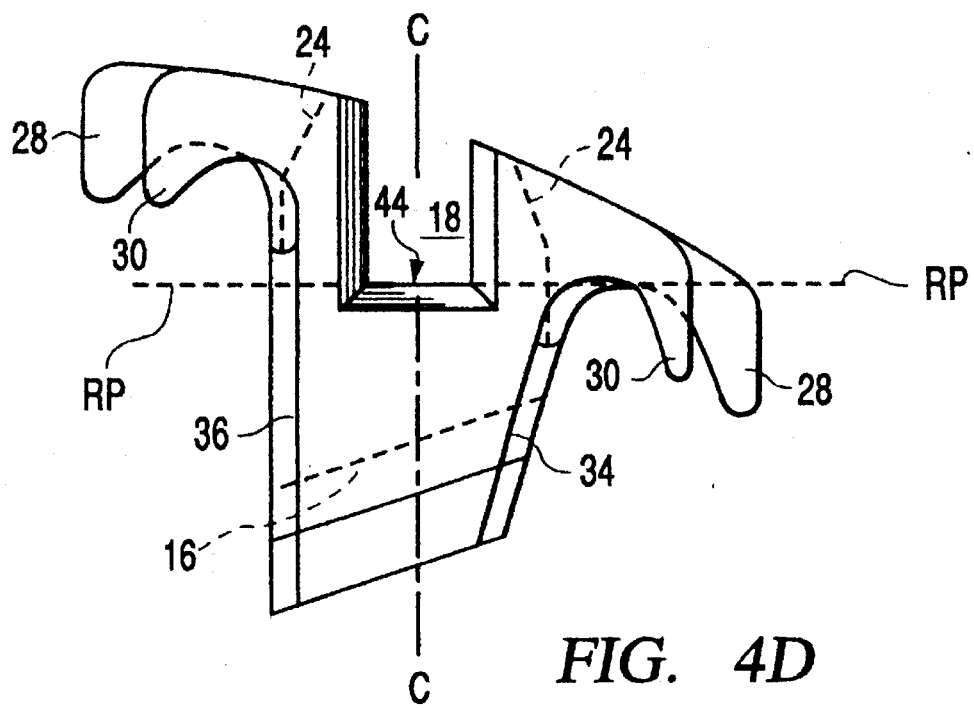
Figure 4E:
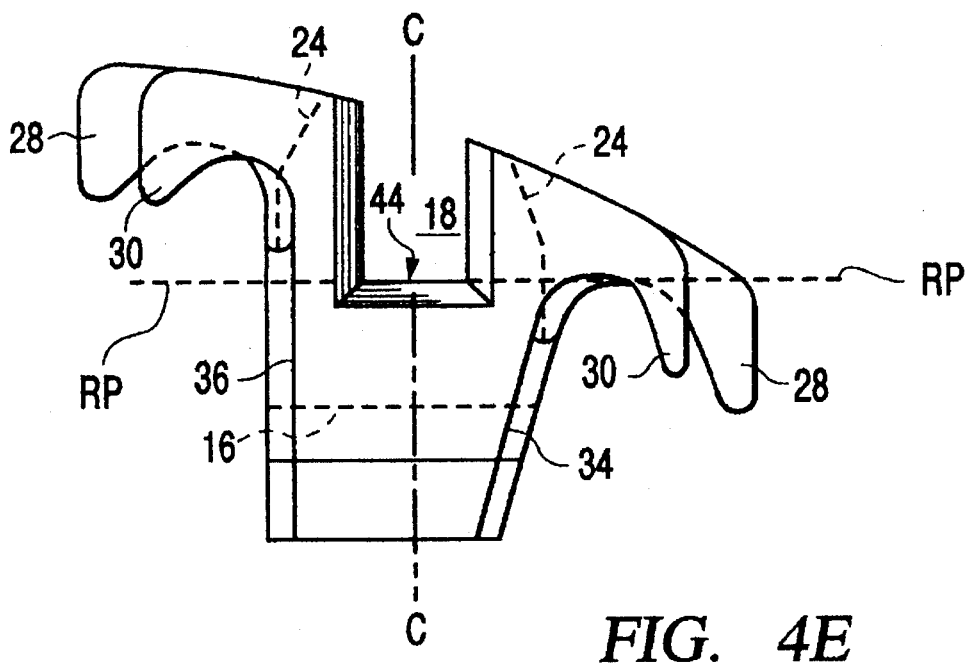

Referring in more detail to FIGS. 4C–E, the trapezoidal configuration of the bracket 10 is illustrated with three alternate configurations for the base portion 16. Generally, the configuration of the base portion 16, namely its occlusal/gingival extent, may be defined in relation to the reference plane RP. As can be seen in FIGS. 4B–E, the reference plane RP coincides with that portion of the bottom or floor of the archwire slot 18 which engages the archwire when positioned therein e.g., a plane which is tangent to the two convex slot floor portions 44.

The configurations of base portion 16 in FIGS. 4C–E allow a practitioner to provide positive, negative, and no torque on a tooth of a particular orientation. Initially, with the tie wing 34 being gingivally positioned in a maxillary application, the base portion 16 of FIG. 4C would be used to provide for "positive torque" on a tooth, the base portion 16 of FIG. 4D would be used to provide for "negative torque" on a tooth, and the base portion 16 of FIG. 4E would be used to provide for "no torque" on a tooth. More particularly, in the case of the bracket 10 of FIG. 4C the base portion 16 would thereby extend from its gingival edge to its occlusal edge generally toward the reference plane RP in order to properly orient the archwire slot 18 on the orthodontic patient. Moreover, in the case of the bracket 10 of FIG. 4D the base portion 16 would thereby extend from its gingival edge to its occlusal edge generally away from the reference plane RP in order to properly orient the archwire slot 18 on the orthodontic patient. Furthermore, in the case of the bracket 10 of FIG. 4E the base portion 16 would thereby extend from its gingival edge to its occlusal edge generally parallel with the reference plane RP in order to properly orient the archwire slot 18 on the orthodontic patient.

In the event that the tie wing 36 is gingivally positioned in a mandibular application, the base portion 16 of FIG. 4C would provide for "negative torque" on the tooth, the base portion 16 of FIG. 4D would provide for "positive torque" on the tooth, and the base portion 16 of FIG. 4E would provide "no torque" on the tooth.

Figure 5A:
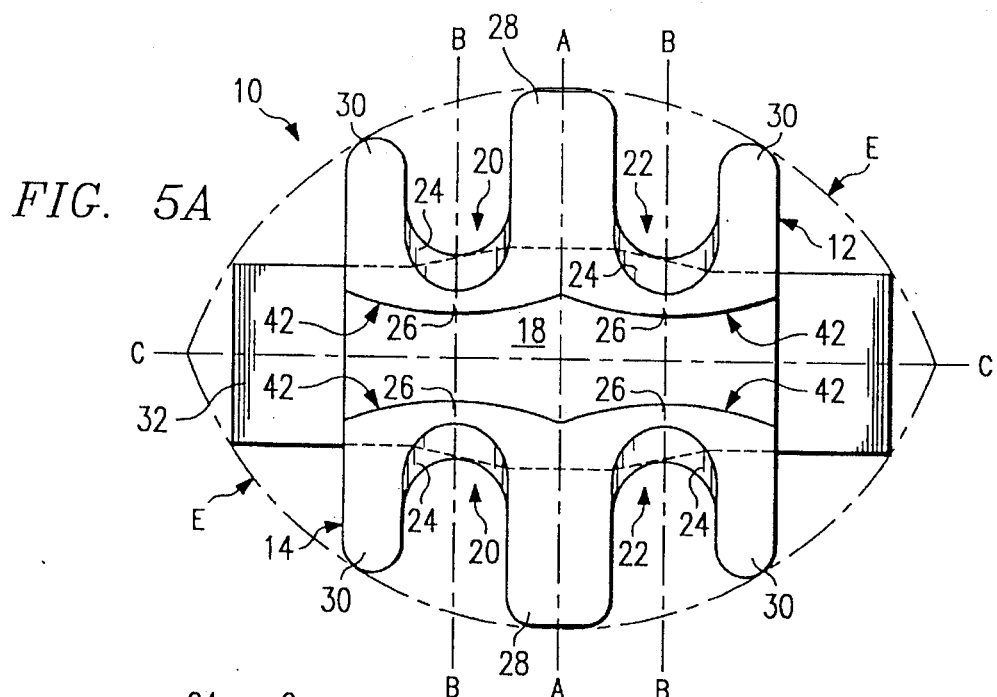
FIGS. 5A–C illustrate labial, side and end views of the modified embodiment of the present invention illustrated in FIGS. 4A–C, with a central auxiliary slot.
Figure 5C:
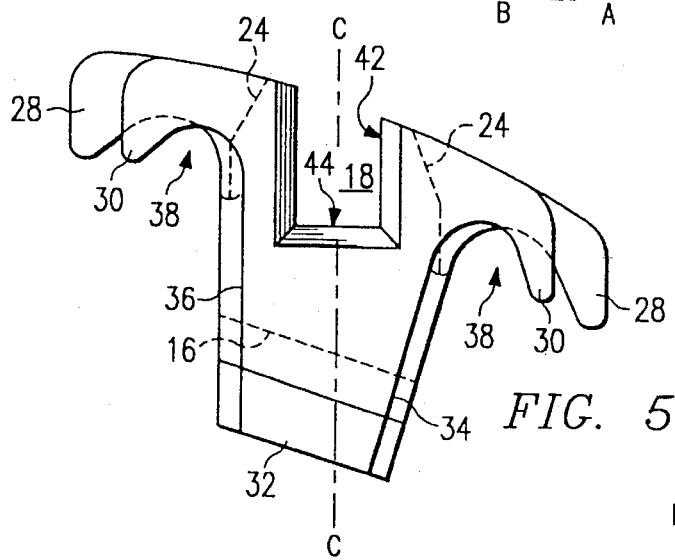
Figure 5B:
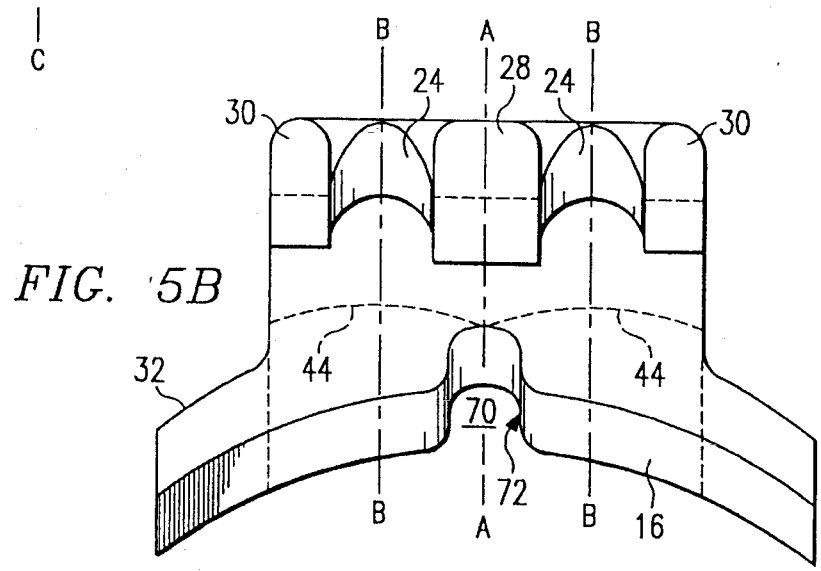

The modified embodiment illustrated in FIGS. 4A–C is shown with additional features in FIGS. 5A–C and 6A–C, although the bracket 10 of FIGS. 4D–E could be similarly modified as well. In FIGS. 5A–C, a central auxiliary slot 70 is provided. FIGS. 6A–C illustrate the inclusion of twin auxiliary slots 80 for receiving of auxiliary devices. The twin vertical slots 80 are disposed so that each passes under one of the convex slot floor portions 44.

In the version shown in FIGS. 6A–C, it should also be appreciated that the gingival-occlusal center axis of the bracket (lying within plane AA) can be disposed at an acute angle relative to center axis of archwire slot 18 (lying within plane CC). More particularly, center legs 28 may be centered upon the gingival-occlusal center axis and may be provided with distal/mesial surfaces 84 which are parallel to the gingival-occlusal center axis thereby facilitating placement of the bracket. In this modified version, it should be recognized that while the center plane BB of the ligating support means 20 is also disposed parallel to the gingival-occlusal center axis, the apices of the convex slot sidewall portions 42 and convex slot floor portion on each of mesial and distal sides lie in a plane which is perpendicular to the archwire slot center plane CC. Relatedly, it should be appreciated that, when a T-shaped hook is utilized (such as the T-shaped hook 50 illustrated in FIGS. 3A–C above), the center axis thereof will be disposed perpendicularly to the center axis of the archwire slot 18 and at an angle relative to the gingival-occlusal center axis of the bracket 10.

The foregoing description of the present invention has been provided for purposes of illustration and description. This description is not intended to limit the invention and various modalities thereof. Variations, embodiments and modifications will be apparent to those skilled in the art and are intended to be within the scope of the following claims.

What is claimed is:

1. An edgewise orthodontic bracket comprising:

gingival and occlusal tie wings defining a labially opening archwire slot therebetween, each of the gingival and occlusal tie wings having a mesial/distal extent, said gingival wing comprising a gingivally-extending center leg and gingivally-extending mesial and distal wing tip portions, wherein said gingivally-extending center leg extends a greater distance from said archwire slot than each of said gingivally-extending mesial and distal wing tip portions, said occlusal wing comprising an occlusally-extending center leg and occlusally-extending mesial and distal wing tip portions, wherein said occlusally-extending center leg extends a greater distance from said archwire slot than each of said occlusally-extending mesial and distal wing tip portions;

a first set of gingival and occlusal notches, the gingival notch being disposed within the mesial/distal extent of said gingival tie wing and the occlusal notch being disposed within the mesial/distal extent of said occlusal tie wing; and a second set of gingival and occlusal notches, the gingival notch being disposed within the mesial/distal extent of said gingival tie wing and the occlusal notch being disposed within the mesial/distal extent of said occlusal tie wing, said first set of notches being disposed on a mesial side of said bracket and said second set of notches being disposed on a distal side of said bracket.

2. An edgewise orthodontic bracket as recited in claim 1, wherein:

gingival edges of said gingival tie wing and occlusal edges of said occlusal tie wing define an elliptical configuration.

3. An edgewise orthodontic bracket as recited in claim 1, further comprising:

a first set of opposing convex sidewall portions and a first convex floor portion within said archwire slot, wherein said first set of convex sidewall portions and said first convex floor portion are positioned substantially between said gingival and occlusal notches of said first set of notches; and, a second set of opposing convex sidewall portions and a second convex floor portion within said archwire slot, wherein said second set of convex sidewall portions and said second convex floor portion are positioned substantially between said gingival and occlusal notches of said second set of notches.

4. An edgewise orthodontic bracket comprising: gingival and occlusal tie wings positioned in opposing relation to define a labially opening archwire slot therebetween;

said gingival tie wing having a gingivally-extending center leg and integral, gingivally-extending mesial and distal tie wing tip portions;

said occlusal tie wing having an occlusally extending center leg and integral, occlusally-extending mesial and distal tie wing tip portions; and a cantilevered, T-shaped hook extending from and integral with the center leg portion of one of said gingival and occlusal tie wings.

5. An edgewise orthodontic bracket as recited in claim 4, said T-shaped hook comprising:

a tapered portion contiguous with said center leg portion of said one of said gingival and occlusal tie wings;

a neck portion contiguous with said tapered portion; and, a head portion contiguous with said neck portion.

6. An edgewise orthodontic bracket comprising:

first and second opposing tie wings defining a labially opening and mesiodistally-extending archwire slot therebetween, said first tie wing having an outer sidewall extending labially away from a longitudinal center plane of said archwire slot, said second tie wing having an outer sidewall extending substantially parallel to said longitudinal center plane of the archwire slot, wherein a trapezoidal configuration is defined between said outer sidewalls.

7. A bracket, as claimed in claim 6, further comprising:

a base, said first and second tie wings extending upwardly from said base.

8. A bracket, as claimed in claim 7, wherein:

said first and second tie wings are positioned on gingival and occlusal sides, respectively, of said archwire slot;

said archwire slot has an archwire engaging bottom portion which is contained within a reference plane; and said base has gingival and occlusal edges, said base extending generally parallel with said reference plane from said gingival to said occlusal edge.

9. A bracket, as claimed in claim 7, wherein:

said first and second tie wings are positioned on gingival and occlusal sides, respectively, of said archwire slot;

said archwire slot has an archwire engaging bottom portion which is contained within a reference plane; and said base has gingival and occlusal edges, said base extending generally toward said reference plane from said gingival edge to said occlusal edge.

10. A bracket, as claimed in claim 7, wherein:

said first and second tie wings are positioned on gingival and occlusal sides, respectively, of said archwire slot;

said archwire slot has an archwire engaging bottom portion which is contained within a reference plane; and said base has gingival and occlusal edges, said base extending generally away from said reference plane from said gingival edge to said occlusal edge.

11. An edgewise orthodontic bracket comprising:

gingival and occlusal tie wings define a labially opening archwire slot therebetween, said archwire slot having opposing sidewalls and an adjoining floor;

a first convex portion extending labially from said floor and across said archwire slot; and, a first auxiliary slot positioned under said convex portion.

12. An edgewise orthodontic bracket as recited in claim 11, further comprising:

a second convex portion extending labially from said floor and across said archwire slot; and, a second auxiliary slot positioned under said second convex portion;

wherein said first convex portion and said first auxiliary slot are located on a mesial side of said bracket, and said second convex portion and said second auxiliary slot are located on a distal side of said bracket.

13. An edgewise orthodontic bracket comprising:

a body comprising gingival and occlusal sidewalls;

gingival and occlusal tie wings extending from said body and defining a labially opening archwire slot therebetween, wherein said gingival and occlusal tie wings are in a fixed position;

an auxiliary slot extending entirely through said body from said occlusal sidewall to said gingival sidewall, wherein said auxiliary slot is positioned on at least one of a mesial and a distal side of said bracket; and, an auxiliary orthodontic treatment device having a shaft portion positionable within said auxiliary slot;

said auxiliary slot and said shaft portion of said auxiliary orthodontic treatment device having complimentary configurations wherein rotational movement therebetween is restricted.

14. An edgewise orthodontic bracket as recited in claim 13, wherein said auxiliary slot comprises adjoining, flat sidewalls, and wherein said shaft portion of said auxiliary device comprises complimentary adjoining, flat outer sidewalls.

15. An edgewise orthodontic bracket as recited in claim 13, wherein said orthodontic treatment device further comprises a portion which extends beyond said gingival tie wing when said orthodontic treatment device is installed in said auxiliary slot.

16. An edgewise orthodontic bracket as recited in claim 13, wherein said auxiliary slot is positioned on a mesial side of said bracket.

17. An edgewise orthodontic bracket as recited in claim 13, wherein said auxiliary slot is positioned on a distal side of said bracket.

18. An edgewise orthodontic bracket as recited in claim 13, wherein said auxiliary slot is positioned on a mesial side of said bracket, said bracket further comprising a second auxiliary slot extending entirely through said body from said occlusal sidewall to said gingival sidewall and a second auxiliary orthodontic treatment device having a shaft portion positionable within said second auxiliary slot, said second auxiliary slot and said shaft portion of said second auxiliary orthodontic treatment device having complimentary configurations wherein rotational movement therebetween is restricted.

19. An orthodontic edgewise bracket as recited in claim 13, wherein said orthodontic treatment device further comprises means for receiving a generally mesio-distally extending force applying member.

20. An orthodontic edgewise bracket as recited in claim 13, wherein an occlusal end of said orthodontic treatment device is positioned within said auxiliary slot, and wherein a gingival end of said orthodontic treatment device has at least one of a mesio and distal facing notch.

21. An orthodontic edgewise bracket as recited in claim 13, wherein said archwire slot has a floor, said body comprises an base which interfaces with a tooth, and said auxiliary slot extends through said base below said archwire slot.

22. An orthodontic bracket, comprising:

a base attachable to a tooth;

a body portion attached to said base and having at least one pair of opposing sidewalls;

gingival and occlusal tie wings extending from said body portion and a defining a labially opening archwire slot therebetween; and first and second displaced auxiliary slots, said first and second auxiliary slots each extending from one of said sidewalls to the other of said sidewalls.

23. An orthodontic bracket as recited in claim 22, wherein said first and second auxiliary slots are substantially parallel, said first auxiliary slot being positioned on a mesial side of said bracket, said second auxiliary slot being positioned on a distal side of said bracket.

24. An orthodontic bracket as recited in claim 22, wherein said archwire slot has a floor and is generally mesially-distally extending.

25. An orthodontic bracket as recited in claim 24, further comprising first and second convex floor portions projecting from said floor of said archwire slot and extending across said archwire slot, said first and second auxiliary slots extending through said first and second convex floor portions, respectively.

26. An edgewise orthodontic bracket comprising:

gingival and occlusal tie wings define a labially opening archwire slot therebetween, said archwire slot having opposing sidewalls and an adjoining floor;

a first convex portion extending labially from said floor and across said archwire slot;

a first auxiliary slot positioned under said convex portion;

a second convex portion extending labially from said floor and across said archwire slot; and, a second auxiliary slot positioned under said second convex portion;

wherein said first convex portion and said first auxiliary slot are located on a mesial side of said bracket, and said second convex portion and said second auxiliary slot are located on a distal side of said bracket.

27. An edgewise orthodontic bracket comprising:

gingival and occlusal tie wings defining a labially opening archwire slot therebetween, each of the gingival and occlusal tie wings having a mesial/distal extent, said gingival tie wing further comprising a gingivally-extending center leg portion and gingivally-extending mesial and distal tie wing tip portions, said occlusal tie wing further comprising an occlusally-extending center leg portion and occlusally-extending mesial and distal tie wing tip portions, wherein gingival edges of said gingival tie wing and occlusal edges of said occlusal tie wing define an elliptical configuration.

* * * * *

(12) EX PARTE REEXAMINATION CERTIFICATE (6394th)
United States Patent
Franseen et al.

(10) Number: US 5,470,228 C1
(45) Certificate Issued: Aug. 26, 2008

(54) EDGEWISE ORTHODONTIC BRACKET

(75) Inventors: Steve A. Franseen, Denver, CO (US); Jeffrey A. Peterson, Aurora, CO (US)

(73) Assignee: RMO, Inc., Denver, CO (US)

Reexamination Request:
No. 90/007,969, Mar. 8, 2006

Reexamination Certificate for:
Patent No.: 5,470,228
Issued: Nov. 28, 1995
Appl. No.: 08/060,879
Filed: May 12, 1993

Related U.S. Application Data

(63) Continuation-in-part of application No. PCT/US92/04263, filed on May 20, 1992.

(51) Int. Cl.
*A61C 7/12* (2006.01)
*A61C 7/00* (2006.01)

(52) U.S. Cl. ............... 433/8; 433/10; 433/13; 433/18

(58) Field of Classification Search .......... None
See application file for complete search history.

(56) References Cited

U.S. PATENT DOCUMENTS

| | | | |
|---|---|---|---|
| 3,028,671 A | 4/1962 | Berger | 32/14 |
| 3,765,091 A | 10/1973 | Northcutt | 32/14 |
| 4,193,195 A | 3/1980 | Merkel et al. | 433/13 |
| 4,197,642 A | 4/1980 | Wallshein | 433/11 |
| 4,478,577 A | 10/1984 | Warren, Jr. | 433/14 |

*Primary Examiner*—Jeanne M. Clark

(57) ABSTRACT

An improved edgewise orthodontic bracket is disclosed. In one embodiment, a bracket (10) comprises a single pair of opposing T-shaped tie wings (12, 14) which define an archwire slot (18) therebetween. Notches (20) are provided on each of the mesial and distal sides of the center leg (28) of each T-shaped tie wing (12, 14) for selectively receiving a ligating device. The notches (20) are defined in the gingival/occlusal edges of the tie wings (12, 14) and comprise sloped portions (24) that extend labially towards the archwire slot (18). Convex sidewall portions (42) and convex floor portions (44) are provided in the archwire slot (18) adjacent to the notches (20). An auxiliary slot (70) may be centrally disposed under the center legs (28) of the opposing T-shaped tie wings (12, 14). Alternatively, twin auxiliary slots (80) may be disposed under the convex archwire slot floor portions (44). An integral T-shaped hook (50) may be provided as a cantilevered extension from the center leg (28) of one of the T-shaped tie wings (12, 14) for use in attachment of traction devices.

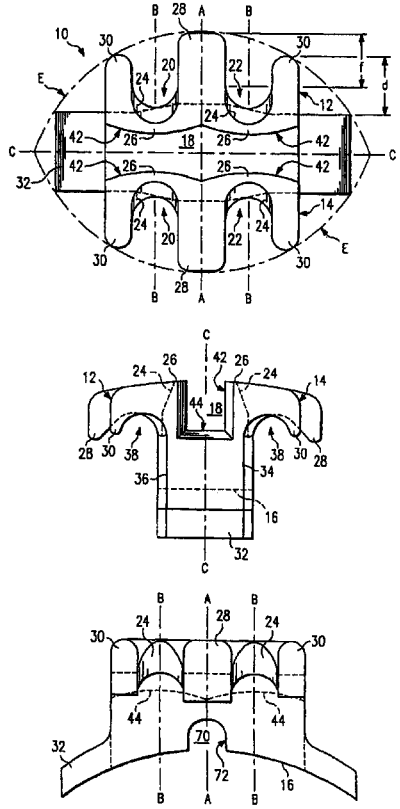

US 5,470,228 C1

EX PARTE
REEXAMINATION CERTIFICATE
ISSUED UNDER 35 U.S.C. 307

THE PATENT IS HEREBY AMENDED AS
INDICATED BELOW.

AS A RESULT OF REEXAMINATION, IT HAS BEEN DETERMINED THAT:

The patentability of claims 1–12 and 25–27 is confirmed.

Claims 13–24 are cancelled.

New claims 28–39 are added and determined to be patentable.

28. An edgewise orthodontic bracket comprising:
a body comprising gingival and occlusal sidewalls;
gingival and occlusal tie wings defining a labially opening archwire slot therebetween, each of the gingival and occlusal tie wings having a mesial/distal extent, said gingival wing comprising a gingivally-extending center leg and gingivally-extending mesial and distal wing tip portions, wherein said gingivally-extending center leg extends a greater distance from said archwire slot than each of said gingivally-extending mesial and distal wing tip portions, said occlusal wing comprising an occlusally-extending center leg and occlusally-extending mesial and distal wing tip portions, wherein said occlusally-extending center leg extends a greater distance from said archwire slot than each of said occlusally-extending mesial and distal wing tip portions;
a first set of gingival and occlusal notches, the gingival notch being disposed within the mesial/distal extent of said gingival tie wing and the occlusal notch being disposed within the mesial/distal extent of said occlusal tie wing; and
a second set of gingival and occlusal notches, the gingival notch being disposed within the mesial/distal extent of said gingival tie wing and the occlusal notch being disposed within the mesial/distal extent of said occlusal tie wing, said first set of notches being disposed on a mesial side of said bracket and said second set of notches being disposed on a distal side of said bracket;
an auxiliary slot extending entirely through said body from said occlusal sidewall to said gingival sidewall, wherein said auxiliary slot is positioned on at least one of a mesial and a distal side of said bracket; and,
an auxiliary orthodontic treatment device having a shaft portion positionable within said auxiliary slot;
said auxiliary slot and said shaft portion of said auxiliary orthodontic treatment device having complimentary configurations wherein rotational movement therebetween is restricted.

29. An edgewise orthodontic bracket as recited in claim 28, further comprising:
a first set of opposing convex sidewall portions and a first convex floor portion within said archwire slot, wherein said first set of convex sidewall portions and said first convex floor portion are positioned substantially between said gingival and occlusal notches of said first set of notches; and
a second set of opposing convex sidewall portions and a second convex floor portion within said archwire slot, wherein said second set of convex sidewall portions and said second convex floor portion are positioned.

30. An edgewise orthodontic bracket comprising:
a body comprising gingival and occlusal sidewalls;
gingival and occlusal tie wings positioned in opposing relation to define a labially opening archwire slot therebetween;
said gingival tie wing having a gingivally-extending center leg and integral gingivally-extending mesial and distal tie wing tip portions;
said occlusal tie wing having an occlusally extending center leg and integral, occlusally-extending mesial and distal tie wing tip portions;
a cantilevered, T-shaped hook extending from and integral with the center leg portion of one of said gingival and occlusal tie wings;
an auxiliary slot extending entirely through said body from said occlusal sidewall to said gingival sidewall, wherein said auxiliary slot is positioned on at least one of a mesial and a distal side of said bracket;
an auxiliary orthodontic treatment device having a shaft portion positionable within said auxiliary slot; and
said auxiliary slot and said shaft portion of said auxiliary orthodontic treatment device having complimentary configurations wherein rotational movement therebetween is restricted.

31. An edgewise orthodontic bracket as recited in claim 30, said T-shaped hook comprising:
a tapered portion contiguous with said center leg portion of said one of said gingival and occlusal tie wings;
a neck portion contiguous with said tapered portion; and,
a head portion contiguous with said neck portion.

32. An edgewise orthodontic bracket comprising:
a body comprising gingival and occlusal sidewalls;
first and second opposing tie wings defining a labially opening and mesiodistally-extending archwire slot therebetween, said first tie wing having an outer sidewall extending labially away from a longitudinal center plane of said archwire slot, said second tie wing having an outer sidewall extending substantially parallel to said longitudinal center plane of the archwire slot, wherein a trapezoidal configuration is defined between said outer sidewalls;
an auxiliary slot extending entirely through said body from said occlusal sidewall to said gingival sidewall, wherein said auxiliary slot is positioned on at least one of a mesial and a distal side of said bracket;
an auxiliary orthodontic treatment device having a shaft portion positionable within said auxiliary slot; and
said auxiliary slot and said shaft portion of said auxiliary orthodontic treatment device having complimentary configurations wherein rotational movement therebetween is restricted.

33. A bracket, as claimed in claim 32, further comprising:
a base, said first and second tie wings extending upwardly from said base.

34. A bracket, as claimed in claim 33, wherein:
said first and second tie wings are positioned on gingival and occlusal sides, respectively, of said archwire slot;
said archwire slot has an archwire engaging bottom portion which is contained within a reference plane; and
said base has gingival and occlusal edges, said base extending generally parallel with said reference plane from said gingival to said occlusal edge.

35. A bracket, as claimed in claim 33, wherein:

said first and second tie wings are positioned on gingival and occlusal sides, respectively, of said archwire slot;

said archwire slot has an archwire engaging bottom portion which is contained within a reference plane; and said base has gingival and occlusal edges, said base extending generally toward said reference plane from said gingival edge to said occlusal edge.

36. A bracket, as claimed in claim 33, wherein:

said first and second tie wings are positioned on gingival and occlusal sides, respectively, of said archwire slot;

said archwire slot has an archwire engaging bottom portion which is contained within a reference plane; and said base has gingival and occlusal edges, said base extending generally away from said reference plane from said gingival edge to said occlusal edge.

37. An edgewise orthodontic bracket comprising:

gingival and occlusal tie wings extending from a body and defining a labially opening archwire slot therebetween, said archwire slot having opposing gingival and occlusal sidewalls and an adjoining floor wherein said gingival and occlusal tie wings are in a fixed position;

a first convex portion extending labially from said floor and across said archwire slot;

an auxiliary slot positioned under said convex portion and extending entirely through said body from said occlusal sidewall to said gingival sidewall, wherein said auxiliary slot is positioned on at least one of a mesial and a distal side of said bracket.

38. An edgewise orthodontic bracket comprising:

gingival and occlusal tie wings that extend from a body and define a labially opening archwire slot therebetween, said archwire slot having opposing gingival and occlusal sidewalls and an adjoining floor;

a first convex portion extending labially from said floor and across said archwire slot;

a second convex portion extending labially from said floor and across said archwire slot;

at least one auxiliary slot positioned under one of said first convex portion or said second convex portion;

wherein said first convex portion is located on a mesial side of said bracket, and said second convex portion is located on a distal side of said bracket;

the at least one auxiliary slot extending entirely through said body from said occlusal sidewall to said gingival sidewall, wherein the at least one auxiliary slot is positioned on one of a mesial and a distal side of said bracket.

39. An edgewise orthodontic bracket comprising:

gingival and occlusal tie wings extending from a body and defining a labially opening archwire slot therebetween, each of the gingival and occlusal tie wings having a mesial/distal extent, said gingival tie wing further comprising a gingivally-extending center leg portion and gingivally-extending mesial and distal tie wing tip portions, said occlusal tie wing further comprising an occlusally-extending center leg portion and occlusally-extending mesial and distal tie wing tip portions, wherein gingival edges of said gingival tie wing and occlusal edges of said occlusal tie wing define an elliptical configuration;

an auxiliary slot extending entirely through said body comprising gingival and occlusal sidewalls, wherein said auxiliary slot is positioned on at least one of a mesial and a distal side of said bracket.

\* \* \* \* \*